(12) United States Patent
Hardin et al.

(10) Patent No.: US 8,287,465 B2
(45) Date of Patent: Oct. 16, 2012

(54) DISPOSABLE AUTOMATED TISSUE EXCISION AND COLLECTION DEVICE

(75) Inventors: Terry D. Hardin, Irvine, CA (US); Brian Dougherty, Terre Haute, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 328 days.

(21) Appl. No.: 12/181,860

(22) Filed: Jul. 29, 2008

(65) Prior Publication Data

US 2010/0030104 A1 Feb. 4, 2010

(51) Int. Cl.
*A61B 10/00* (2006.01)
*A61B 17/32* (2006.01)
*A61B 17/14* (2006.01)
*A61B 17/34* (2006.01)

(52) U.S. Cl. ........ 600/565; 600/562; 600/563; 600/564; 600/566; 600/567; 600/568; 606/167; 606/179; 606/180; 606/181; 606/182; 606/184; 606/185

(58) Field of Classification Search .......... 600/562–568; 606/167, 179–182, 184, 185
See application file for complete search history.

(56) References Cited

U.S. PATENT DOCUMENTS

| 4,051,852 | A | * | 10/1977 | Villari ........................... 604/183 |
| 5,133,359 | A | * | 7/1992 | Kedem .......................... 600/567 |
| 5,156,160 | A | * | 10/1992 | Bennett ......................... 600/567 |
| 5,306,237 | A | * | 4/1994 | Clement et al. ................. 604/30 |
| 5,817,033 | A | * | 10/1998 | DeSantis et al. ............. 600/562 |
| 6,638,235 | B2 | * | 10/2003 | Miller et al. .................. 600/566 |
| 6,652,522 | B2 | * | 11/2003 | Cucin ............................ 606/49 |
| 7,458,940 | B2 | * | 12/2008 | Miller ........................... 600/568 |
| 7,517,321 | B2 | * | 4/2009 | McCullough et al. ........ 600/566 |
| 7,806,834 | B2 | * | 10/2010 | Beckman et al. ............. 600/566 |
| 8,057,402 | B2 | * | 11/2011 | Hibner et al. ................. 600/566 |
| 2007/0149895 | A1 | * | 6/2007 | McCullough et al. ........ 600/566 |

* cited by examiner

*Primary Examiner* — Max Hindenburg
*Assistant Examiner* — Devin Henson
(74) *Attorney, Agent, or Firm* — Vista IP Law Group LLP (57) ABSTRACT

An biopsy apparatus includes a pressure and vacuum generator including a first cylinder and a first piston movably disposed within the cylinder. The cylinder has a pressure generating region and a vacuum generating region. The biopsy apparatus also includes an outer cannula and an inner cannula having a lumen. The inner cannula is movably disposed within the outer cannula, and the vacuum generating region is in one-way fluid communication with the inner cannula lumen.

17 Claims, 7 Drawing Sheets

DISPOSABLE AUTOMATED TISSUE EXCISION AND COLLECTION DEVICE

TECHNICAL FIELD

The disclosure generally relates to devices for performing biopsies.

BACKGROUND

Many existing vacuum assisted biopsy systems operate while connected to an external control panel and power source. Many spring-loaded core-biopsy devices require the user to perform a large number of actions. First, the user must manually prepare the biopsy device by squeezing, pulling, or rotating a lever. Tissue acquisition is then initiated by pressing one or more buttons. To retrieve the tissue, the user must repeat some or all of the manual preparation steps. Similarly, acquiring additional cores requires additional manual steps. What is needed is a compact tissue sampling device that is self-contained and operable with a minimum number of manual actions of a user.

BRIEF DESCRIPTION OF THE DRAWINGS

Referring now to the drawings, illustrative embodiments are shown in detail. Although the drawings represent some embodiments, the drawings are not necessarily to scale and certain features may be exaggerated, removed, or partially sectioned to better illustrate and explain the present invention. Further, the embodiments set forth herein are exemplary and are not intended to be exhaustive or otherwise limit or restrict the claims to the precise forms and configurations shown in the drawings and disclosed in the following detailed description.

DETAILED DESCRIPTION

Figure 1:
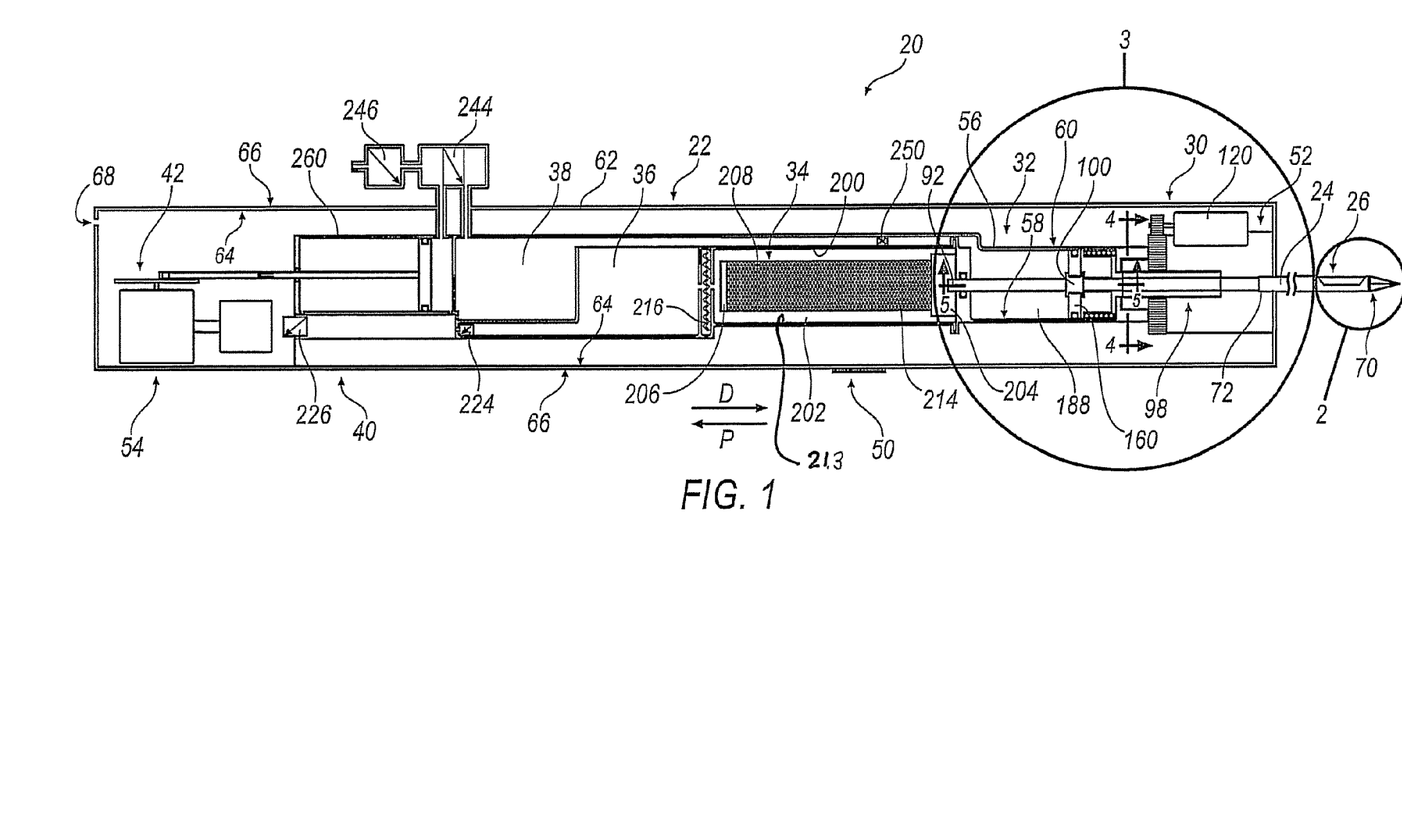
FIG. 1 is a biopsy device, according to an exemplary embodiment.

FIG. 1 illustrates a biopsy device 20. The biopsy device 20 includes a housing 22, an outer cannula 24 extending from the housing 22, an inner cannula 26 interposed within the outer cannula 24, a rotary assembly 30 operably coupled to the inner cannula 26, an axial translation assembly 32 operably coupled to the inner cannula 26, a sample collection portion 34, a vacuum accumulator 36, a positive pressure accumulator 38, a pressure and vacuum generating portion, or pressure and vacuum generator, 40, and a pressure portion power source 42. As discussed in greater detail below, the pressure and vacuum generator 40 may be self-contained within the housing 22, thereby eliminating capital equipment such as external vacuum pumps.

The housing 22 encloses many of the components of the device 20 and includes a control portion 50 for controlling operation of the device 20. The housing 22 includes a first distal end 52, a second proximal end 54, an inner wall 56 having an inner wall inner surface 58 and an inner wall outer surface 60, a first outer wall 62 having a first outer wall inner surface 64 and a first outer wall outer surface 66, and a vent 68.

Figure 2:
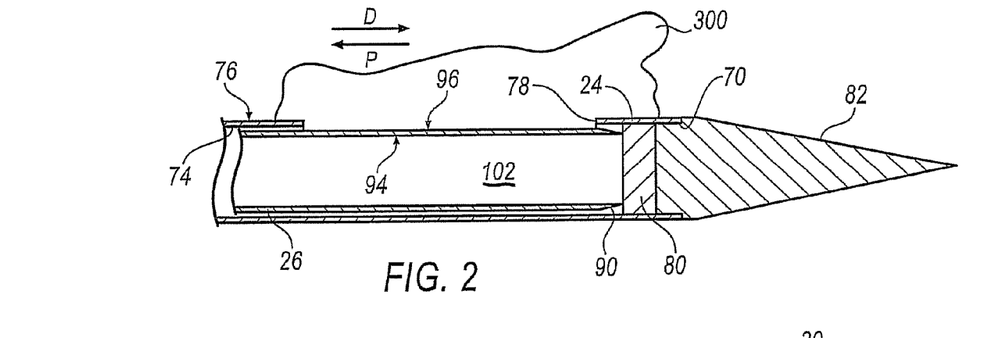
FIG. 2 is an enlarged view of an inner and outer cannula in a first configuration.

As best seen in FIGS. 1 and 2, the outer cannula 24 includes a first distal outer cannula end 70, a second proximal outer cannula end 72, an outer cannula inside surface 74, an outer cannula outer surface 76, a distal opening, or lateral opening, 78, a cutting board 80, and a tip 82 at the first outer cannula end 70. In the embodiment illustrated, the tip 82 is a trocar tip, although other tips may be used. The inner cannula 26 includes a first distal inner cannula end 90, a second proximal inner cannula end 92, an inner cannula inside surface 94, an inner cannula outer surface 96, an inner cannula rotary coupling portion 98, and an inner cannula axial coupling portion 100. Inner cannula 26 also includes a lumen 102 for aspirating tissue samples through inner cannula 26 for collection in sample collection portion 34.

In the embodiment illustrated, the inner cannula 26 is rotatably and axially moveable within the outer cannula 24 as the outer cannula 24 remains generally stationary relative to the housing 22. Also in the embodiment illustrated, the first distal inner cannula end 90 (FIG. 2) is sharpened to provide a tissue severing portion for the inner cannula 26.

Figure 3:
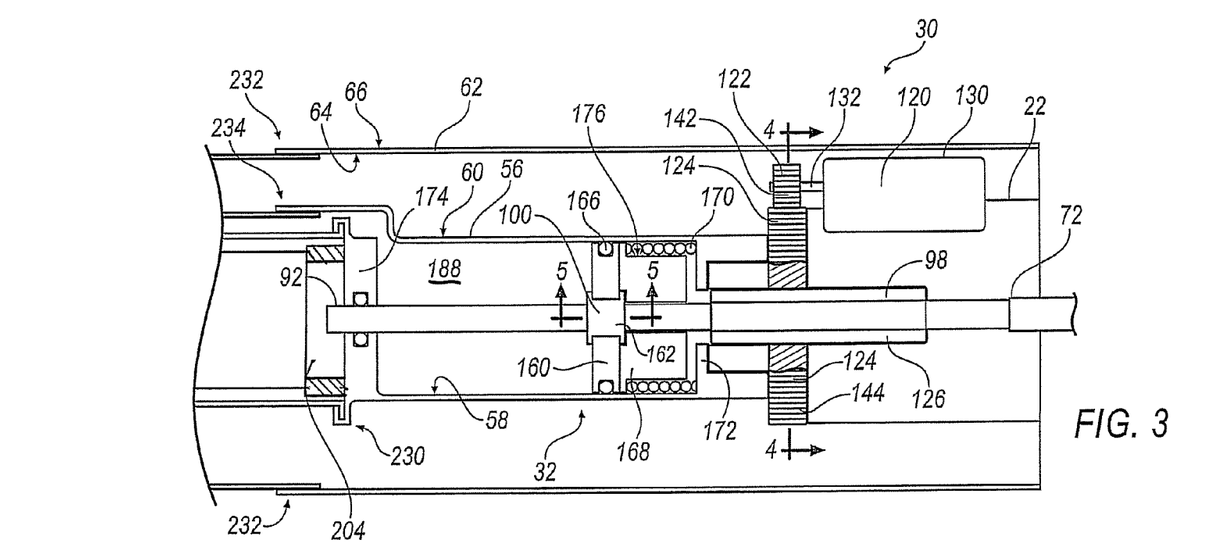
FIG. 3 is a partially sectioned enlarged view of a distal end portion of FIG. 1.
Figure 4:
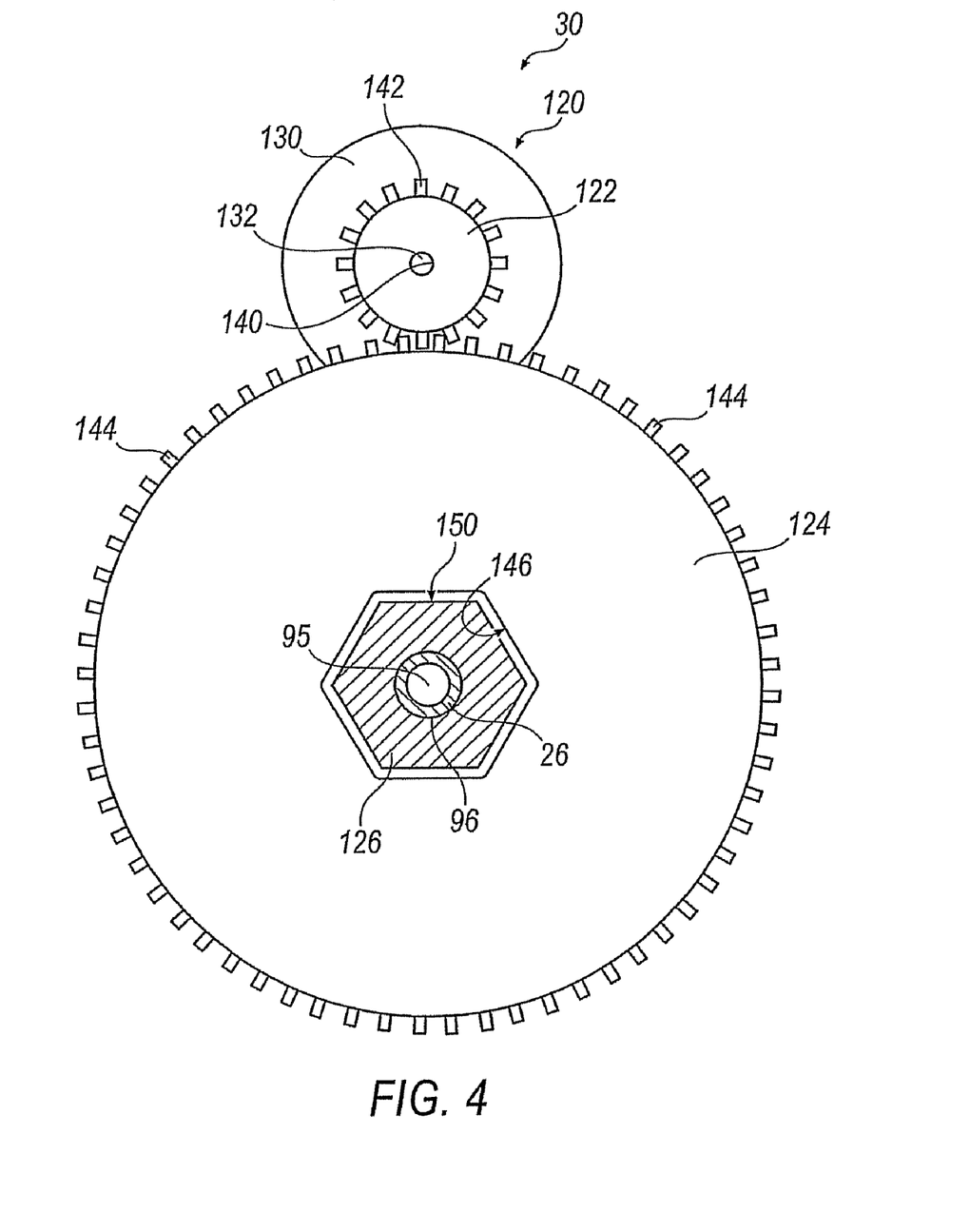
FIG. 4 is a partial sectional view taken along line 4-4 of FIG. 3.

As best seen in FIG. 3, the rotary assembly 30 includes a rotation motor 120, a pinion gear 122, a spur gear 124, and a sliding coupler 126. The rotation motor 120 includes a rotation motor housing 130 and a shaft 132. As best seen in FIG. 4, the pinion gear 122 includes an inner surface 140 coupled for rotation with the shaft 132, and a plurality of pinion gear teeth 142. The spur gear 124 includes a plurality of spur gear teeth 144 and a contoured inner surface 146. The sliding coupler 126 includes contoured outer surface 150 for mating with the contoured inner surface 146 and a sliding coupler inner surface coupled to the inner cannula outer surface 96. Rotation of the motor 120 will rotate the pinion gear 122, the spur gear 124, the sliding coupler 126, and the inner cannula 26. The sliding coupler 126 is operably coupled to the inner cannula 26 for rotation therewith while permitting the inner cannula 26 and the sliding coupler 126 to move axially (proximally and distally) relative to the spur gear 124. While the exemplary embodiment illustrates both the contoured inner surface 146 and the contoured outer surface 150 as generally hexagonal, other appropriate shapes may be used.

Figure 5:
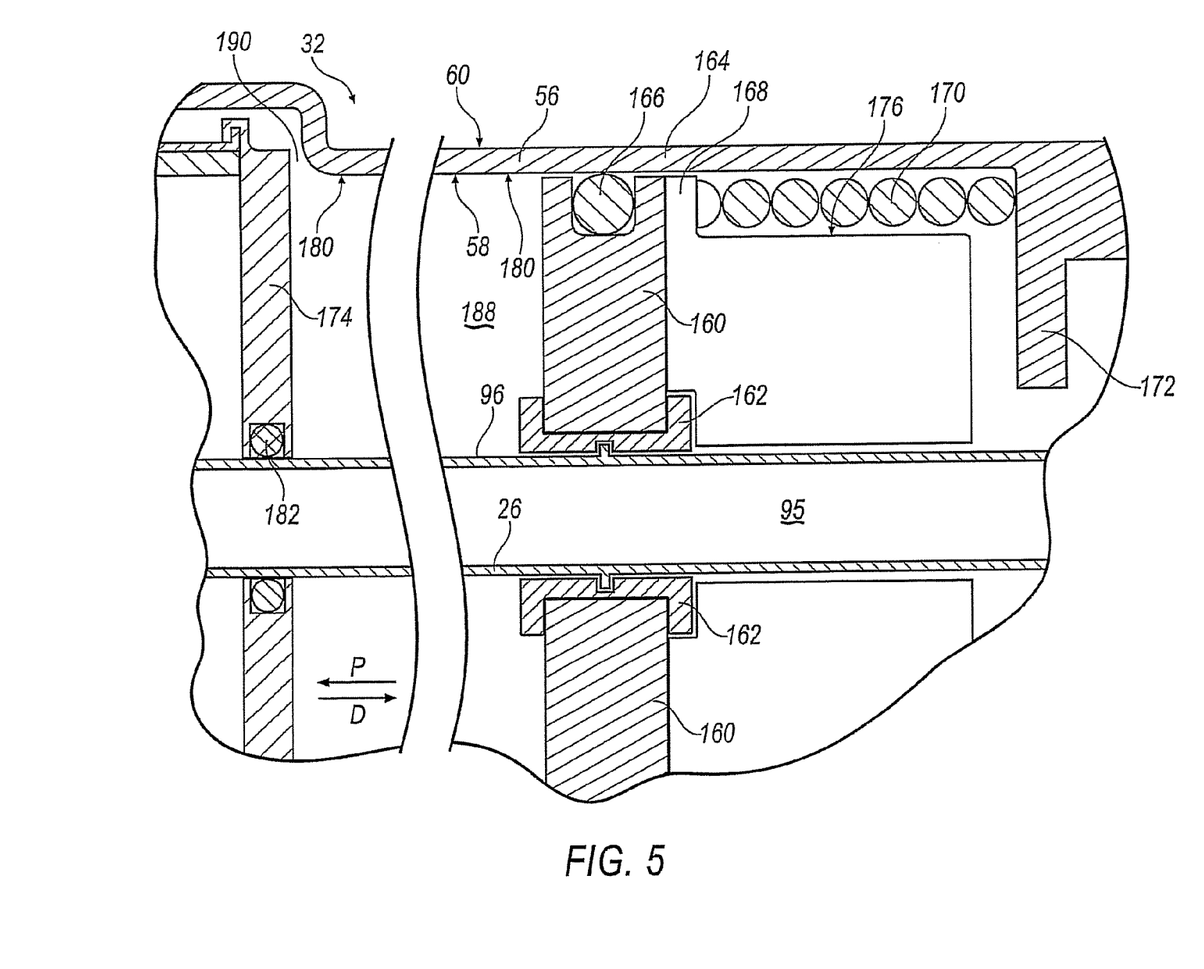
FIG. 5 is a partial sectional view taken along line 5-5 of FIG. 3.

As best seen in FIG. 5, the axial translation assembly 32 is a hydraulic motor or actuator that includes an axial piston 160 coupled to the inner cannula 26 with a rotating coupling 162, an axial sleeve portion 164, a piston seal 166 in sliding contact with the axial sleeve portion 164, a spring guide 168, a spring 170, a distal sleeve wall 172, and a proximal sleeve wall 174. In the embodiment illustrated, the spring guide 168 is a generally cylindrical extension of the axial piston 160 that has an outer cylindrical surface 176 where the surface 176 guides the spring 170 during compression and extension with the intent of preventing an undesirable overlap of any portions of the spring 170, although the spring guide 168 may be omitted. The axial piston 160 is coupled to the inner cannula 26 (via the rotating coupling 162) such that axial piston 160 is restricted from moving axially relative to inner cannula 26 while allowing the inner cannula 26 to rotate relative to the axial piston 160. The axial sleeve portion 164 (which may be a portion of the housing 22 inner wall 56) includes an axial sleeve portion inner surface 180. The piston seal 166 contacts the axial sleeve portion inner surface 180 of the axial sleeve portion 164 while providing a generally sealed connection between the axial piston 160 and the axial sleeve portion inner surface 180. The spring 170 provides a biasing force Fs (between the distal sleeve wall 172 and the axial piston 160) that urges the axial piston 160 (and the inner cannula 26) generally toward the direction P (FIG. 1) relative to the distal sleeve wall 172. The proximal sleeve wall 174 includes a proximal seal 182 coupled to the inner cannula 26 to permit relative rotation and axial translation between the proximal seal 182 and the inner cannula 26. The axial piston 160, the piston seal 166, the proximal sleeve wall 174, the proximal seal 182, and the axial sleeve portion 164 form an axial translation assembly chamber 188 having a port 190 formed in the proximal sleeve wall 174. As discussed in greater detail below, as a fluid (not shown) is forced into the axial translation assembly chamber 188 through the port 190, the axial piston 160 is forced in the general direction of the arrow D (FIG. 1), and as the fluid is exhausted from the axial translation assembly chamber 188 through the port 190 and through exhaust valve 250 (discussed in greater detail below), the spring 170 will urge the axial piston 160 generally in the direction of the arrow P.

Figure 6:
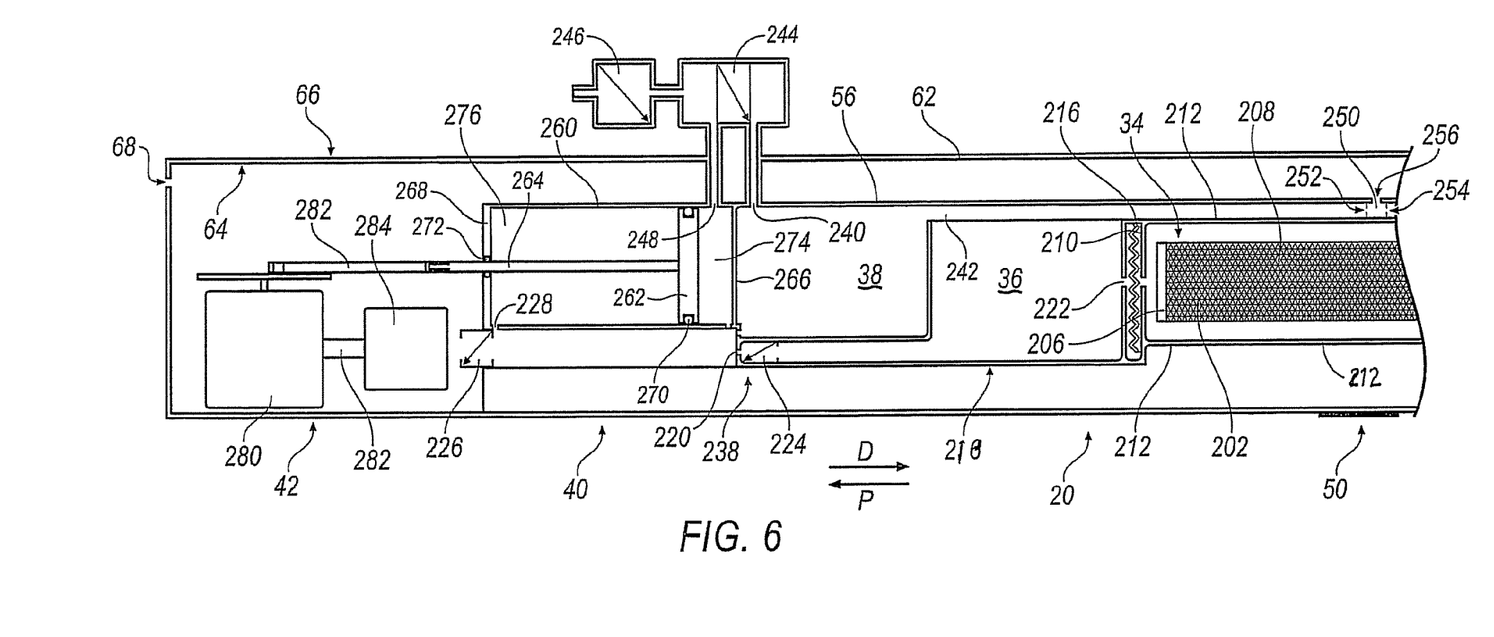
FIG. 6 is an enlarged view of a portion of FIG. 1.

As best shown in FIGS. 1 and 6, the sample collection portion 34 includes a collection canister 200 having an inside volume 202, and a tissue collection filter 213 comprising a base portion 204, an end cap 206, and a screen portion 208. The screen portion 208 is a generally cylindrical tube of material having the end cap 206 attached to a generally circular end and the base portion 204 attached to an opposing generally circular end. Generally, the tissue collection filter 213 may be removed from the sample collection portion 34.

Generally, the screen portion 208 will permit air and fluids to flow through the collection canister while retaining the samples within the collection canister 200. The sample collection portion 34 is defined by a sample collection end wall 210, a sample collection outer wall 212, and the proximal sleeve wall 174. The screen portion 208 defines an inner screen volume 214 for retaining tissue samples, as discussed in greater detail below. The inner screen volume 214 is in fluid communication with the inner cannula lumen 102 at the second inner cannula end 92 such that biopsy samples that are transferred through the inner cannula 26 will enter the inner screen volume 214 of the collection canister 200. A filter member 216 is positioned between the sample collection end wall 210 and the vacuum accumulator 36. Generally, the filter member 216 is semipermeable to the extent that the filter member 216 will not inhibit the flow of gasses but will inhibit the flow of fluids. As an illustrative example, the filter member 216 may be a semipermeable membrane or a liquid resistant layer (including a material such as Gore Tex®) that permits gases to pass therethrough while inhibiting the flow of blood and other bodily fluids. In the embodiment illustrated, the housing 22 is sufficiently proportioned to accommodate all fluids collected during the use of the device 20, although in other embodiments, a separate fluid collection container may be used. In one embodiment, the inside volume 202 of the collection canister is sized to retain the fluids collected during use of the device 20.

Referring to FIG. 6, a vacuum system 218 includes the vacuum accumulator 36, a first vacuum port 220, a second vacuum port 222, a first vacuum unidirectional flow valve 224, a second vacuum unidirectional flow valve 226, and a vacuum port 228. The vacuum accumulator 36 is generally sealed with the exception of the first vacuum port 220 and the second vacuum port 222 and may be defined, at least in part, by the inner wall 56 of the housing 22. The first vacuum unidirectional flow valve 224 and the second vacuum unidirectional flow valve 226 will permit fluid (generally air) to exit the vacuum accumulator 36.

As best seen in FIG. 3, the collection canister 200 includes a removable connection 230 to permit the collection canister 200 to be disassembled for removal of the tissue collection filter 213 and samples contained therein, as discussed in greater detail below. Base portion 204 is removably attached to proximal sleeve wall 174 to allow tissue collection filter 213 to be removed from collection canister 200. Additionally, the first outer wall 62 includes a disassembly joint portion 232 and the inner wall 56 includes a disassembly joint portion 234 to provide access to collection canister 200.

With continued reference to FIG. 6, a pressure system 238 includes the positive pressure accumulator 38, a pressure inlet 240, a pressure outlet 242, a first pressure unidirectional flow valve 244, a second pressure unidirectional flow valve 246, a pressure port 248, and an exhaust valve 250. The pressure accumulator 38 is generally sealed with the exception of the pressure inlet 240 and the pressure outlet 242 and may be defined, at least in part, by the inner wall 56 of the housing 22. The first pressure unidirectional flow valve 244 and the second pressure unidirectional flow valve 246 will permit fluid (generally air) to enter the pressure accumulator 38. Although in the embodiment illustrated the first pressure unidirectional flow valve 244 and the second pressure unidirectional flow valve 246 are illustrated outside the first outer wall 62 for clarity of illustration, the first pressure unidirectional flow valve 244 and the second pressure unidirectional flow valve 246 may be positioned entirely within the first outer wall 62. The exhaust valve 250 will permit fluid to exhaust from the axial translation assembly chamber 188.

In the embodiment illustrated, the exhaust valve 250 is a three way valve controlled by the control portion 50 such that the exhaust valve 250 will permit fluid to exhaust from the axial translation assembly chamber 188 while preventing fluid from exhausting from the pressure accumulator 38. Specifically, exhaust valve 250 includes an inlet port 252, a supply port 254, and a vent 256. The exhaust valve 250 is operable in a first configuration where the inlet port 252 is in fluid communication with the supply port 254 while the vent 256 is not in fluid communication with either the inlet port 252 or the supply port 254 and in a second configuration where the vent 256 is in fluid communication with the supply port 254 while the inlet port 252 is not in fluid communication with either the vent 256 or the supply port 254.

The vacuum accumulator 36 and the pressure accumulator 38 provide the device 20 with two chambers for assisting the pressure and vacuum generator 40 in operation. That is, the pressure accumulator 38 will accumulate compressed fluid supplied to the pressure accumulator 38 during operation of the pressure and vacuum generator 40 (discussed below). This accumulation of fluid within the pressure accumulator 38 will permit the device 20 to supply fluid in a more consistent flow that does not depend upon the instantaneous flow capacity of the pressure and vacuum generator 40. Further, a portion of any gasses within the vacuum accumulator 36 will be removed during operation of the pressure and vacuum generator 40 (as discussed in greater detail below) as the first distal inner cannula end 90 of the inner cannula 26 is generally in contact with the cutting board 80. This removal of gasses from the vacuum accumulator 36 (and from the sample collection portion 34) will provide a suction at the first distal inner cannula end 90 of the inner cannula 26, as discussed in greater detail below, that is greater than the instantaneous flow capacity of the pressure and vacuum generator 40.

As best seen in FIGS. 1 and 6, the pressure and vacuum generator 40 includes a cylinder, or sleeve portion, 260, a piston 262, a piston rod 264, a first (distal) sleeve portion end wall 266, a second (proximal) sleeve portion end wall 268, a piston seal 270 interposed between the piston 262 and the sleeve portion 260, and a rod seal 272 interposed between the piston rod 264 and the second sleeve portion end wall 268. In the embodiment illustrated, the sleeve portion 260 includes a first end, or pressure generating region, 274 at the distal side of the piston 262 and a second end, or vacuum generating region, 276 at the proximal side of the piston 262. The pressure port 248 is formed in the first end 274 and the vacuum port 228 is formed in the second end 276.

The vacuum accumulator 36 of the vacuum system 218 is in fluid communication with the inner cannula lumen 102 such that the vacuum (decrease in pressure) created within the vacuum generating region 276 will decrease the pressure within the inner cannula lumen 102, as discussed in greater detail below.

The pressure portion power source 42 includes a pump motor 280, a connecting rod 282 pivotally connected to the piston rod 264, and a power supply 284. Rotation of the pump motor 280 will cause the piston 262 to reciprocate within the sleeve portion 260. In the embodiment illustrated, the power supply 284 is operably connected to the pump motor 280, the exhaust valve 250, and the rotation motor 120 through the control portion 50, although other arrangements, such as individual power supplies, may be included. Further, the exhaust valve 250 may be manually actuated.

Figure 7:
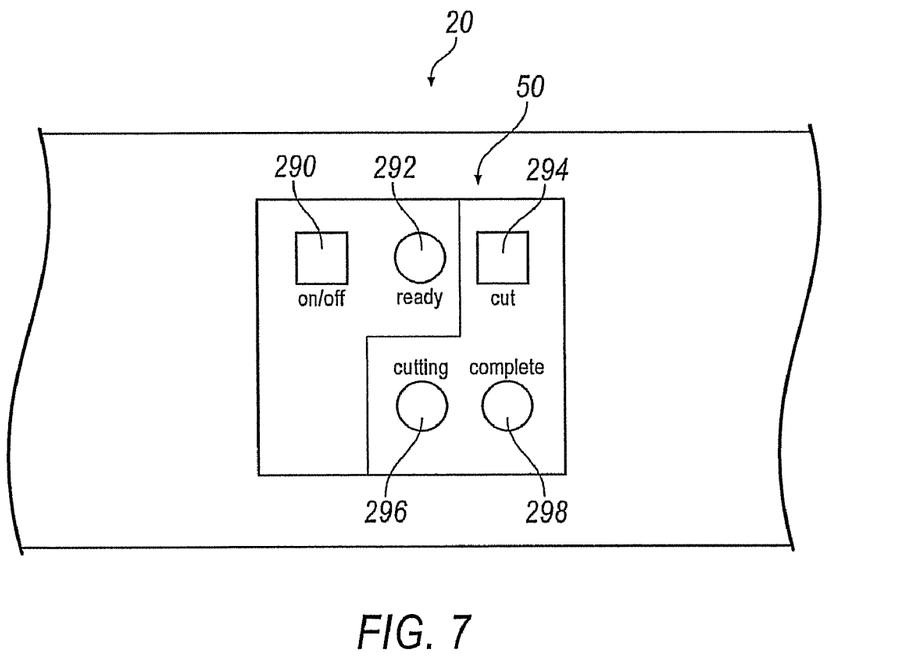
FIG. 7 is a view of a control portion for the device of FIG. 1.

The control portion 50 may be positioned on the housing 22 and may include controls and indications for controlling the operation of the device 20. The control portion 50 may include a microprocessor other control means for performing the operations described herein. In the embodiment of FIG. 7, the control portion 50 includes a power switch 290, a power indication 292, a biopsy switch 294, a cutting indication 296, and a complete indication 298.

In operation, a user will prepare the patient, remove the device 20 from a sterile package (not shown) and actuate the power switch 290. Device 20 is first operated in a pressure and vacuum generating mode. When the power switch 290 is actuated, the pump motor 280 will reciprocate the piston 262 within the sleeve portion 260. Reciprocation of the piston 262 within the sleeve portion 260 will increase the pressure within the pressure accumulator 38 and decrease the pressure within the vacuum accumulator 36. In this illustrative example, the exhaust valve 250 is in the first configuration where the inlet port 252 is in fluid communication with the supply port 254 while the vent 256 is not in fluid communication with either the inlet port 252 or the supply port 254, thus permitting pressure to increase within the pressure accumulator 38 and urge the axial piston 160 toward the distal direction D (FIG. 5).

Decreasing the pressure within the vacuum accumulator 36 will create a vacuum within the inner cannula 26. With the exhaust valve 250 in the first configuration, increasing the pressure within the pressure accumulator 38 (and the axial translation assembly chamber 188) will force the axial piston 160 and the inner cannula 26 generally in the direction D until the first distal inner cannula end 90 of the inner cannula 26 contacts the cutting board 80. In the embodiment illustrated, the piston 262 will continue to reciprocate within the sleeve portion 260 after the pressure accumulator 38 and the vacuum accumulator 36 have reached 'equilibrium' pressures, although the piston 262 may be stopped until further operation is desired (such as when the pressure in the pressure accumulator 38 decreases or when the pressure in the vacuum accumulator 36 increases). These 'equilibrium' pressures are reached and generally not exceeded since slip of fluid (generally air) past the piston seal 270 will limit the maximum pressure within the pressure accumulator 38 and limit the minimum pressure within the vacuum accumulator 36.

When the device 20 is operated in the pressure and vacuum generating mode, and the piston 262 moves within the sleeve portion 260 toward the pressure accumulator 38, fluid is forced through the valve 244 from the pressure generating region 274 toward the pressure accumulator 38. As the piston 262 moves within the sleeve portion 260 away from the pressure accumulator 38, fluid is drawn through the valve 246 toward the pressure generating region 274 within the sleeve portion 260. Then, as the piston 262 returns toward the pressure accumulator 38, the fluid that entered through the valve 246 is forced through the valve 244 from the pressure generating region 274 toward the pressure accumulator 38. In this manner, operation of the pressure and vacuum generator 40 will supply fluid to the pressure accumulator 38 with each movement of the piston 262 toward the pressure accumulator 38. However, as the pressure within the pressure accumulator 38 builds, the movement of the piston 262 toward the pressure accumulator 38 may result in some amount of fluid slipping past the seal 270 from the pressure generating region 274 to the vacuum generating region 276. This slip may prevent any further movement of fluid toward the pressure accumulator 38 which may result in the equilibrium pressure for the pressure accumulator 38.

As piston 262 moves toward the second sleeve portion end wall 268, fluid in the vacuum generating portion 276 is forced out of the vacuum port 228, the second vacuum unidirectional flow valve 226, and the vent 68. As the piston 262 moves away from the second sleeve portion end wall 268, fluid in the vacuum accumulator 36 will exit the valve 224, thereby decreasing the pressure within the vacuum accumulator 36. At least a portion of the fluid expelled from the valve 224 will then be expelled from the valve 226 and vent 68 as the piston 262 moves toward the wall 268. The vent 68 permits a flow of air into and out of the housing 22, as the pressure and vacuum generator 40 operates.

When the pressure accumulator 38 and the vacuum accumulator 36 have reached 'equilibrium' pressures, the indication 292 may illuminate to notify the user that the device 20 is ready for sampling. The time required to generate desired pressures for sampling operations of the device 20 may be a few seconds, or longer, depending upon factors such as the speed of the pump motor 280. Further, unidirectional pressure regulator valves may be included in lieu of either valve 244 or 224 to limit the pressures of the pressure accumulator 38 and/or the vacuum accumulator 36, as desired.

When the indication 292 illuminates to notify the user that the device 20 is ready for sampling, the user may operate the device 20 in a tissue sampling cutting and collecting mode. The user first inserts the outer cannula 24 into a patient and positions the lateral opening 78 of the outer cannula 24 adjacent to a desired tissue 300 (FIG. 2). At this point, the lateral opening 78 is sealed from the tissue 300 by the inner cannula 26, as shown in FIG. 2 and the axial piston 160 is in a distal most position, as shown in FIG. 1. The user may then actuate the biopsy switch 294 to initiate a sampling operation. When the biopsy switch 294 has been actuated, the rotation motor 120 will begin to rotate the inner cannula 26 and the exhaust valve 250 (FIGS. 1 and 6) will exhaust fluid from the axial translation assembly chamber 188 to a portion of the device 20 outside of the pressure accumulator 38 (as the exhaust valve 250 is reconfigured to the second configuration where the vent 256 is in fluid communication with the supply port 254 while the inlet port 252 is not in fluid communication with either the vent 256 or the supply port 254). In one example, the fluid is exhausted to the annular space between the inner wall 56 and the first outer wall 62 where the fluid may be subsequently expelled through the vent 68. Exhausting fluid from the axial translation assembly chamber 188 (while preventing fluid from transferring from the pressure accumulator 38 to the axial translation assembly chamber 188) will permit the axial piston 160 to move generally in the direction of the arrow P as the spring 170 urges both the axial piston 160 and the inner cannula 26 toward the collection canister 200 (generally in the direction of the arrow P), as shown in FIG. 8.

Figure 8:
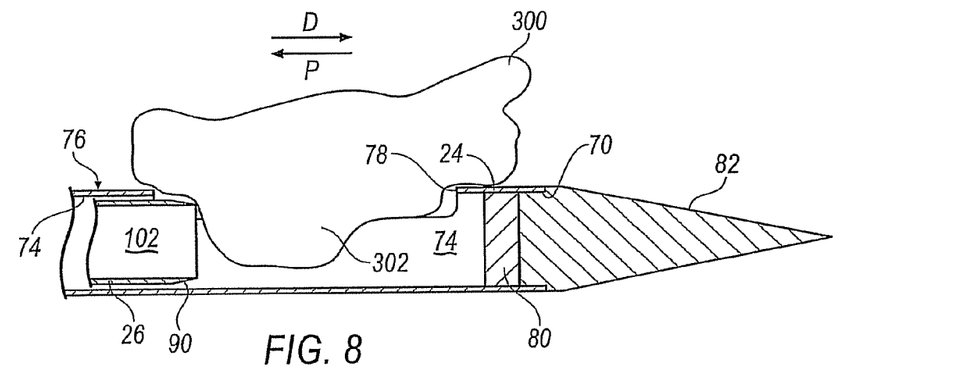
FIG. 8 is a view similar to FIG. 2, illustrating the device in a second configuration.
Figure 9:
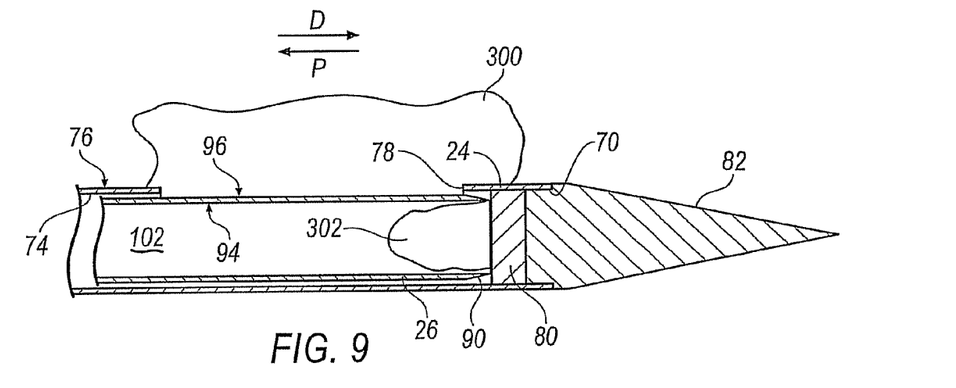
FIG. 9 is a view similar to FIG. 2, illustrating the device in a third configuration.

As best seen in FIG. 8, when the inner cannula 26 moves in the direction of the arrow P, the first distal inner cannula end 90 of the inner cannula 26 moves past the lateral opening 78 of the outer cannula 24 to allow a portion 302 of the desired tissue 300 to prolapse within the lateral opening 78. As a portion of the desired tissue 300 prolapses into the lateral opening 78, the negative pressure generated in the vacuum accumulator 36 will encourage the portion 302 to remain within the inner cannula. After the inner cannula 26 has moved in the direction of the arrow P (generally after the first distal inner cannula end 90 of the inner cannula 26 moves past the lateral opening 78 of the outer cannula 24) and the tissue portion 302 has entered the outer cannula 24, the exhaust valve 250 is reconfigured to the first configuration (where the inlet port 252 is in fluid communication with the supply port 254 while the vent 256 is not in fluid communication with either the inlet port 252 or the supply port 254) and the inner cannula 26 is then moved in the direction of the arrow D as the fluid from the pressure accumulator again urges the axial piston 160 in the direction D. Specifically, to move the inner cannula 26 in the direction of the arrow D, the control portion 50 will manipulate the exhaust valve 250 such that fluid (air) is permitted to flow from the pressure accumulator 38 toward the axial translation assembly chamber 188, thereby increasing the pressure within the axial translation assembly chamber 188. Increasing the pressure within the axial translation assembly chamber 188 will force the axial piston 160 and the inner cannula 26 generally in the direction D until the first distal inner cannula end 90 of the inner cannula 26 contacts the cutting board 80, thereby severing the tissue portion 302 between the first distal inner cannula end 90 of the inner cannula 26 and the cutting board 80. This tissue portion 302 is then urged through the inner cannula 26 into the collection canister 200 by the lower pressure within the vacuum accumulator 36. The indicator 298 may then indicate to the user that the tissue portion 302 has been harvested, or the user may view the tissue portion through a clear portion of the housing 22. The user may then collect additional samples of tissue in a similar manner. When samples are collected, the tissue collection filter 213 may be removed by disassembling removable connection 230, the disassembly joint portion 232 and the disassembly joint portion 234, thereby permitting access to the tissue collection filter 213. In one embodiment, the tissue collection filter 213 may be removed from the device 20, while in other embodiments, the filter 213 may be accessed such that tissue portions, such as the tissue portion 302, may be removed.

To move the inner cannula 26 in the direction of the arrows P and D, the control portion 50 may time the movement by actuating the exhaust valve 250 to vent the axial translation assembly chamber 188, waiting a predetermined amount of time sufficient to permit the first distal inner cannula end 90 of the inner cannula 26 to move past the lateral opening 78 of the outer cannula 24, and then actuate the exhaust valve 250 to permit fluid from the pressure accumulator 38 to enter the axial translation assembly chamber 188 to force the inner cannula 26 generally in the direction D until the first distal inner cannula end 90 of the inner cannula 26 contacts the cutting board 80 to sever tissue.

The outer wall 212 of the sample collection portion 34, the vacuum accumulator, 36, the positive pressure accumulator 38, the sleeve portion 260 may be formed as an integral portion of the housing 22. The housing 22 may be a handpiece for grasping with a single hand or a table mounted housing, as desired. If the housing is table mounted, such as for a magnetic resonance imaging (MRI) assisted sample, the outer cannula 24 may be rotatable relative to the housing 22 to permit samples to be taken radially with respect to the outer cannula.

In the exemplary embodiment illustrated, both the outer cannula 24 and the inner cannula 26 are formed of a surgical grade metal. Most preferably, the outer cannula 24 and the inner cannula 26 are formed of stainless steel. In the case of an MRI compatible device, the outer cannula 24 and the inner cannula 26 can be formed of an Inconel, Titanium or other materials with similar magnetic characteristics. Likewise, the trocar tip 82 is most preferably formed of stainless steel honed to a sharp tip. The trocar tip 82 can be suitably bonded to the outer cannula 24, such as by welding or the use of an appropriate adhesive. In some embodiments, the inner and outer cannulae can be formed of a non-metallic material of appropriate strength and stiffness.

The valves 224, 226, 244, and 246, while described as unidirectional, may be any device that permits the flow of fluid as described herein, including check valves and stop-check valves or other suitable devices.

As used herein, "vacuum" may or may not refer to a perfect vacuum (0.0 psia). A partial vacuum refers to a relative pressure that is between atmospheric pressure and a perfect vacuum. Also as used herein, the term "pressure" refers to a fluid with a relative pressure above atmospheric. Generally, when a user removes the device 20 from a sterile package, the pressure in both the vacuum accumulator 36 and the pressure accumulator 38 is atmospheric pressure.

Although the steps of the method of operating the device 20 are listed in an exemplary order, the steps may be performed in differing orders or combined such that one operation may perform multiple steps. Furthermore, a step or steps may be initiated before another step or steps are completed, or a step or steps may be initiated and completed after initiation and before completion of (during the performance of) other steps.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope. The scope of the invention is limited solely by the following claims.

What is claimed is:

1. A biopsy apparatus, comprising:
a pressure and vacuum generator including a first cylinder and a first piston movably disposed within the cylinder, wherein the cylinder has a pressure generating region and a vacuum generating region;
an outer cannula;
an inner cannula having a lumen;
a hydraulic actuator operably coupled to the inner cannula;
a pressure accumulator including a first chamber fluidly connected to the pressure and vacuum generator and fluidly disposed between the pressure and vacuum generator and the hydraulic actuator; and
a vacuum accumulator including a second chamber fluidly connected to the pressure and vacuum generator and fluidly disposed between the pressure and vacuum generator and the inner cannula,
wherein the inner cannula is movably disposed within the outer cannula and the vacuum generating region is in one-way fluid communication with the inner cannula lumen to substantially prevent fluid from passing from the vacuum generating region to the vacuum accumulator, the pressure generating region is in one-way fluid communication with the pressure accumulator to substantially prevent fluid from passing from the pressure accumulator to the pressure generating region, the pressure accumulator is in selective fluid communication with the hydraulic actuator, and the vacuum accumulator is in fluid communication with the lumen.

2. The biopsy apparatus of claim 1, further comprising at least one motor for rotating and axially translating the inner cannula within the outer cannula.

3. The biopsy apparatus of claim 1, wherein the first piston separates the vacuum generating region from the pressure generating region, and movement of the first piston within the first cylinder changes the volume of the vacuum generating region and the pressure generating region.

4. The biopsy apparatus of claim 1, further comprising a first vacuum valve having an inlet in fluid communication with the vacuum accumulator and an outlet in fluid communication with the vacuum generating region, wherein the first vacuum valve allows air to flow from the inlet to the outlet and substantially prevents air from flowing from the outlet to the inlet.

5. The biopsy apparatus of claim 4, wherein the first vacuum valve is a one-way valve.

6. The biopsy apparatus of claim 1, wherein the hydraulic actuator comprises a second cylinder and a second piston movably disposed within the second cylinder, the second piston is operably coupled to the inner cannula, the inner cannula is rotatable with respect to the second piston, and axial translation of the second piston causes the inner cannula to axially translate.

7. The biopsy apparatus of claim 1, further comprising a first pressure valve having an inlet in fluid communication with the pressure generating region and an outlet in fluid communication with the pressure accumulator, wherein the first pressure valve allows air to flow from the inlet to the outlet and substantially prevents air from flowing from the outlet to the inlet.

8. The biopsy apparatus of claim 1, further comprising a rotary motor and a reciprocating motor operatively connected to the inner cannula, wherein operation of the rotary motor causes the inner cannula to rotate, and operation of the reciprocating motor causes the inner cannula to translate axially.

9. The biopsy apparatus of claim 1, further comprising a tissue collection filter, wherein the tissue collection filter is substantially impermeable to tissue samples, and when the biopsy apparatus is in a tissue sample collection mode, the tissue collection filter receives unfiltered tissue samples from the inner cannula lumen.

10. The biopsy apparatus of claim 9, wherein when the biopsy apparatus is in the tissue sample collection mode, air flows from the tissue collection filter to a vacuum accumulator, and liquid is substantially prevented from flowing from the tissue collection filter to the vacuum accumulator.

11. The biopsy apparatus of claim 1, wherein the apparatus has a pressure and vacuum generating mode and a tissue cutting mode.

12. The biopsy apparatus of claim 11, wherein when the apparatus is in the pressure and vacuum generating mode and the first piston moves in a first direction, air is expelled from the vacuum generating region.

13. The biopsy apparatus of claim 12, wherein when the apparatus is in the pressure and vacuum generating mode and the first piston moves in a second direction, air is expelled from the pressure generating region.

14. A biopsy apparatus, comprising:
an outer cannula;
a handheld housing connected to the outer cannula, the handheld housing including:
an inner cannula,
a hydraulic actuator operably coupled to the inner cannula,
a pressure and vacuum generator,
a pressure accumulator including a first chamber fluidly connected to the pressure and vacuum generator and fluidly disposed between the pressure and vacuum generator and the hydraulic actuator, and
a vacuum accumulator including a second chamber fluidly connected to the pressure and vacuum generator and fluidly disposed between the pressure and vacuum generator and the inner cannula,
wherein the pressure and vacuum generator includes a cylinder and a piston movably disposed within the cylinder, the cylinder has a pressure generating region and a vacuum generating region, the inner cannula has a lumen, the vacuum generating region is in one-way fluid communication with the vacuum accumulator to substantially prevent fluid from passing from the vacuum generating region to the vacuum accumulator, the pressure generating region is in one-way fluid communication with the pressure accumulator to substantially prevent fluid from passing from the pressure accumulator to the pressure generating region, the pressure accumulator is in selective fluid communication with the hydraulic actuator, the vacuum accumulator is in fluid communication with the lumen, and the inner cannula is axially translatable and rotatable within the outer cannula.

15. A method of performing a biopsy, comprising:
providing a biopsy apparatus having
an outer cannula having a tissue receiving port,
an inner cannula with a lumen,
a hydraulic actuator operably coupled to the inner cannula,
a pressure accumulator including a first chamber fluidly connected to the pressure and vacuum generator and fluidly disposed between the pressure and vacuum generator and the hydraulic actuator,
a vacuum accumulator including a second chamber fluidly connected to the pressure and vacuum generator and fluidly disposed between the pressure and vacuum generator and the inner cannula, and a pressure and vacuum generator, the pressure and vacuum generator having a cylinder, a piston movably disposed within the cylinder, a vacuum generating region in one-way fluid communication with the vacuum accumulator to substantially prevent fluid from passing from the vacuum generating region to the vacuum accumulator, and a pressure generating region in one-way fluid communication with the pressure accumulator to substantially prevent fluid from passing from the pressure accumulator to the pressure generating region, wherein the pressure accumulator is in selective fluid communication with the hydraulic actuator, and the vacuum accumulator is in fluid communication with the lumen;

operating the biopsy apparatus in a pressure and vacuum generating mode by reciprocating the piston within the pressure and vacuum generator cylinder;

inserting the outer cannula into a patient adjacent a tissue sample; and operating the biopsy apparatus in a tissue sample cutting mode.

16. The method of claim 15, wherein the step of operating the biopsy apparatus in a tissue sample cutting mode comprises translating the inner cannula in the proximal direction to expose the lumen to the tissue sample, whereby the tissue sample prolapses into the tissue receiving port.

17. The method of claim 16, wherein the step of operating the biopsy apparatus in a tissue sample cutting mode comprises rotating the inner cannula within the outer cannula, translating the inner cannula within the outer cannula in the distal direction while continuing to rotate the inner cannula by placing the pressure generating region in fluid communication with the hydraulic actuator, and aspirating the tissue sample in the proximal direction within the lumen.

* * * * *